US008828977B2

(12) United States Patent
Zahos

(10) Patent No.: US 8,828,977 B2
(45) Date of Patent: Sep. 9, 2014

(54) METHOD OF TREATING A SUBJECT SUFFERING FROM DEGENERATIVE DISC DISEASE USING A MATRIX METALLOPROTEASE INHIBITOR

(75) Inventor: Peter A. Zahos, Weston, FL (US)

(73) Assignee: Discogen, LLC, Weston, FL (US)

( * ) Notice: Subject to any disclaimer, the term of this patent is extended or adjusted under 35 U.S.C. 154(b) by 632 days.

(21) Appl. No.: 11/707,315

(22) Filed: Feb. 16, 2007

(65) Prior Publication Data

US 2007/0190149 A1 Aug. 16, 2007

Related U.S. Application Data

(60) Provisional application No. 60/773,666, filed on Feb. 16, 2006, provisional application No. 60/800,838, filed on May 17, 2006.

(51) Int. Cl.
*A61K 31/65* (2006.01)
*A61K 31/164* (2006.01)

(52) U.S. Cl.
USPC .......................................... 514/152; 514/164

(58) Field of Classification Search
USPC ................................................ 514/152, 613
See application file for complete search history.

(56) References Cited

U.S. PATENT DOCUMENTS

| 6,319,910 B1 | 11/2001 | Amin et al. |
| 2004/0147445 A1 | 7/2004 | Levin |
| 2004/0192658 A1 | 9/2004 | Hunter et al. |

FOREIGN PATENT DOCUMENTS

| WO | WO 2005/000283 A2 | 1/2005 |
| WO | WO 2005000283 A2 * | 1/2005 |
| WO | WO 2006/128100 A2 | 11/2006 |

OTHER PUBLICATIONS

International Search Report issued by the International Searching Authority (ISA/US) in connection with International Application No. PCT/US07/04262.
Written Opinion of the International Searching Authority issued by the International Searching Authority (ISA/US) in connection with International Application No. PCT/US07/04262.
International Preliminary Report on Patentability issued by the International Bureau of WIPO in connection with International Application No. PCT/US07/04262.
Communication from the Search Division of the European Patent Office dated Jun. 22, 2011 in connection with European Patent Application No. 07751050.1.
Supplementary European Search Report issued by the Search Division of the European Patent Office on Jun. 6, 2011 in connection with European Patent Application No. 07751050.1.

* cited by examiner

*Primary Examiner* — Sreeni Padmanabhan
*Assistant Examiner* — Jody Karol
(74) *Attorney, Agent, or Firm* — John P. White; Cooper & Dunham LLP

(57) ABSTRACT

The present invention provides a method for treating a vertebrate subject suffering from a degenerative disc disease by administering an inhibitor of a matrix metalloprotease (MMP) to the subject in an amount effective to treat the subject.

9 Claims, No Drawings

METHOD OF TREATING A SUBJECT SUFFERING FROM DEGENERATIVE DISC DISEASE USING A MATRIX METALLOPROTEASE INHIBITOR

This application claims the benefit of U.S. Provisional Application Nos. 60/773,666, filed Feb. 16, 2006, and 60/800,838, filed May 17, 2006, the contents of which are hereby incorporated by reference into this application.

Throughout this application, various references are identified by authors and full citations or by reference to the numbers of U.S. patents or Published Patent Applications. The disclosures of these references in their entireties are hereby incorporated by reference into this application to more fully describe the state of the art to which this invention pertains.

BACKGROUND OF THE INVENTION

The human spine is formed from twenty-six consecutive vertebrae. Each of these vertebrae is separated from any adjacent vertebra by an intervertebral disc that functions to absorb shock and prevent each vertebra from directly impacting upon another vertebra. At the center of each disc is a nucleus pulposus that contains proteoglycan. Around the nucleus pulposus is an outer ring called the annulus fibrosus. THE MERCK MANUAL OF DIAGNOSIS AND THERAPY 1478-1499 (Mark H. Beers and Robert Berkow eds., 17th ed. 1999).

Degenerative disc disease refers to any of the common degenerative conditions of the lower spine involving degeneration of the disc. Disc degeneration is often associated with the symptom of pain and may lead to inflammation and neuropathic pain, for example, spinal stenosis, spondylolisthesis, and retrolisthesis. THE MERCK MANUAL OF DIAGNOSIS AND THERAPY 475-478 (Mark H. Beers and Robert Berkow eds., 17th ed. 1999).

Disc degeneration associated with the aging process is generally associated with the loss of proteoglycan from the nucleus pulposus of the spinal discs and a reduction of the disc's ability to absorb shock between vertebrae. Although some affected patients may not exhibit symptoms, many affected patients suffer from chronic back and/or leg pain. Pain associated with disc degeneration may become debilitating and may greatly reduce a patient's quality of life. THE MERCK MANUAL OF DIAGNOSIS AND THERAPY 1488-1490 (Mark H. Beers and Robert Berkow eds., 17th ed. 1999).

While nonoperative treatments for disc degeneration exist, many patients, for example, those patients with severe symptoms, may not respond to nonoperative treatment. Conventional operative treatment generally involves spondylosyndesis (spinal fusion), which is highly invasive and is associated with certain risks to the patient. THE MERCK MANUAL OF DIAGNOSIS AND THERAPY 1488-1490 (Mark H. Beers and Robert Berkow eds., 17th ed. 1999).

While the biological mechanisms of degenerative disc disease are not well known, it is known that proteoglycans, which are abundant in the disc's nucleus, decline in content with age, are believed to be an important factor in the pathogenesis of the disease. Degenerated and herniated discs are known to produce increased amounts of proteins such as nitric oxide (NO), cytokines, such as interleukin-1 (IL-1 and IL-1β), interleukin-6 (IL-6) and TNF-alpha, prostaglandin E2 ($PGE_2$) and matrix metalloproteases (MMP). These proteins play a regulatory role in the interactions between the biochemical agents produced by degenerated discs. Le Maitre, C. L., et al. (2004) "Localization of degradative enzymes and their inhibitors in the degenerate human invertebral disc," J. Pathol 204:47-54.

Potential therapeutic molecules can be classified as inflammatory mediators, anticatabolics, mitogens, and chondrogenic morphogens. Inflammatory mediators can include TNF-alpha agonists or antagonists such as infliximab (remicade) and etanercept; TNF-alpha stimulated gene-6 (TSG-6); IL-1 receptor antagonists (IL-1R); regulators of IL-6, IL-8, and IL-10; NF-κB inhibitors; MCP-1 inhibitors, and selective COX-2 inhibitors such as rofecoxib and nimesulide. Anticatabolic therapeutics include tissue inhibitors of matrix metalloproteases (TIMPs), such as TIMP-1 and -3, and the biphosphonates clodronate and pamidronate. Mitogens include insulin-like growth factor-1 (IGF-1), platelet-derived growth factor-1 (PGF), epidermal growth factor (EGF), fibroblast growth factor (FGF), and hyaluronan. Chodrogenic morphogens include transforming growth factor-beta (TGF-beta) and growth and differentiation factor-5 (GDF-5). Other possible enzymes for inhibition are those with a disintegrin and metalloproteinase with thrombospondin motif (AD-AMTS) and aggrecanase. Roberts, S., et al. (2000) "Matrix Metalloproteinases and Aggrecanase," SPINE 25(23):3005-3013. Chemically modified tetracyclines have been shown to inhibit both production and activity of various members of the MMP family of enzymes. Fingleton, B. (2003) "CMT-3 CollaGenex," Current Opinion in Investigational Drugs 4(12): 1460-1467; U.S. Pat. No. 6,946,453, issued Sep. 20, 2005 (Ashley, et al.); U.S. Pat. No. 6,894,036, issued May 17, 2005 (Ashley, et al.); U.S. Pat. No. 6,638,922, issued Oct. 28, 2003 (Ashley, et al.); U.S. Pat. No. 5,773,430, issued Jun. 30, 1998 (Simon, et al.).

SUMMARY OF THE INVENTION

This invention provides a method for treating a vertebrate subject suffering from a degenerative disc disease which comprises administering to the subject an inhibitor of a matrix metalloprotease (MMP) inhibitor in an amount effective to treat the subject. Examples of such inhibitors include homologs and analogs of tetracycline, particularly 4-dedimethylaminotetracycline derivatives.

This invention also provides a method for alleviating symptoms of a degenerative disc disease in a subject which comprises administering to the subject an effective symptom alleviating amount of an inhibitor of a matrix metalloprotease.

DETAILED DESCRIPTION OF THE INVENTION

The present invention provides a method for treating a vertebrate subject suffering from a degenerative disc disease which comprises administering to the subject an inhibitor of a matrix metalloprotease (MMP) inhibitor in an amount effective to treat the subject.

As used herein, "matrix metalloprotease" or "MMP" means a zinc-dependent endopeptidase containing a pro-peptide domain, and a catalytic domain connected to a C-terminal domain by a flexible hinge region. Examples of MMPs include, but are not limited to, MMP-1 (interstitial collagenase), MMP-2 (gelatinase-A), MMP-3 (Stromelysin 1), MMP-4, MMP-5, MMP-6, MMP-7 (Matrilysin), MMP-8 (neutrophil collagenase), MMP-9 (gelatinase-B), MMP-10 (Stromelysin 2), MMP-11 (Stromelysin 3), MMP-12 (Macrophage metalloelastase), MMP-13 (collagenase 3), MMP-14, MMP-15, MMP-16, MMP-17, MMP-18 (collagenase 4), MMP-19 (RASI-1), MMP-20 (Enamelysin), MMP-21 (X-MMP), MMP-22, MMP-23, MMP-24, MMP-25, MMP-26 (Matrilysin-2), MMP-27, MMP-28 (Epilysin), and MMP- 29. In one embodiment of the invention, the matrix metalloprotease inhibitor is selected from the aforementioned group.

In one embodiment of the invention, the matrix metalloprotease is MMP-1. In one embodiment of the invention, the matrix metalloprotease is MMP-2. In one embodiment of the invention, the matrix metalloprotease is MMP-3. In one embodiment of the invention, the matrix metalloprotease is MMP-7. In one embodiment of the invention, the matrix metalloprotease is MMP-8. In one embodiment of the invention, the matrix metalloprotease is MMP-9. In one embodiment of the invention, the matrix metalloprotease is MMP-13. In a specific embodiment, the matrix metalloprotease is one or more of MMP-1, MMP-2, MMP-3, MMP-7, MMP-8, MMP-9, and/or MMP-13.

In one embodiment of the invention, the inhibitor is an inhibitor of MMP-2, MMP-8, MMP-9, and/or MMP-13.

In one embodiment of the invention, the amount effective to treat the subject is an amount effective to slow or preferably to inhibit progression of the degenerative disc disease.

In another embodiment of the invention, the amount effective to treat the subject is an amount effective to provide symptomatic relief to the subject, for example, to reduce the pain concomitant with the degenerative disc disease.

In various embodiments of the invention, the inhibitor is a homolog or analog of tetracycline. In one embodiment of the invention, the homolog or analog of tetracycline is a 4-dedimethyltetracycline derivative.

In one embodiment of the invention, the inhibitor is selected from the group consisting of 4-dedimethylaminotetracycline, 4-dedimethylaminosancycline(6-demethyl-6-deoxy-4-dedimethylaminotetracycline), 4-dedimethylaminominocycline(7-dimethylamino-4-dedimethylaminotetracycline), and 4-dedimethylaminodoxycycline(5-hydroxy-6-deoxy-4-dedimethylaminotetracycline).

In one embodiment, the inhibitor is a 4-dedimethylaminotetracycline(6-demethyl-6-deoxy-4-dedimethylaminotetracycline) derivative.

In various embodiments, the inhibitor is administered as a component of a composition which comprises a pharmaceutically acceptable carrier.

In one embodiment of the invention, the pharmaceutically acceptable carrier comprises a biopolymer, such as hyaluronic acid or a pharmaceutically acceptable salt or ester thereof, e.g. sodium hyaluronate.

In one embodiment of the invention, the pharmaceutically acceptable carrier comprises a hydrogel, such as an acrylate polymer.

In such a composition, the inhibitor is present within the carrier at a concentration between 0.1% and 5.0% by weight, preferably, between 0.1% and 1.0% by weight.

In the practice of the invention, the inhibitor is typically administered in conjunction with a surgical procedure which results in the intervertebral discs of the subject being accessible to the inhibitor, e.g. laminectomy or microdiscectomy. Alternatively, the inhibitor is administered by means of a needle or a cannula.

In connection with the invention, the amount of the inhibitor administered to the subject is generally between 0.1 mg/kg and 30 mg/kg body weight of the subject. For certain inhibitors the amount is preferably between 0.3 mg/kg and 10 mg/kg body weight of the subject and the concentration of the inhibitor is typically between 0.1 to 1000 micromolar, preferably between 1.0 to 100 micromolar.

For other inhibitors, the amount of the inhibitor administered to the subject is generally between 1.0 mg/kg and 30 mg/kg body weight of the subject, preferably between 1.0 mg/kg and 10 mg/kg body weight of the subject and the concentration of the inhibitor is typically between 1.0 to 1000 micromolar, preferably between 5.0 to 100 micromolar.

In practice the inhibitor may be administered at any given site once daily or more typically periodically, e.g. weekly, biweekly, or monthly over a period of 30-180 days.

As used herein, a "vertebrate subject" means any subject having a segmented spinal column. Examples include mammals, for example a rabbit, pig, rat, or dog, and primates, for example a monkey, chimpanzee, orangutan, or a human.

As used herein, a "degenerative disc disease" means any condition which results in degeneration of an intervertebral disc, including but not limited to, conditions caused by a disease, physical impact, mechanical wear, a pathogen, or an autoimmune response.

As used herein, "biopolymer" means any polymeric chemical manufactured by a living organism, e.g. proteins and polysaccharides as well as such substances when prepared by chemical syntheses. Many biopolymers spontaneously "fold" into characteristic shapes (also referred to as secondary structure and tertiary structure), which determine their biological function and depend in a complicated way on the primary structure of the biopolymer.

As used herein, "hydrogel" means a natural or synthetic water-soluble polymer, in which water is the dispersion medium. Hydrogels are sometimes found as colloidal gels where water is the dispersion medium. Examples of common ingredients in hydrogels include, but are not limited to, polyvinyl alcohol, sodium polyacrylate, acrylate polymers, and copolymers with an abundance of hydrophilic groups.

As used herein, "homolog or analog of tetracycline" means a compound with a structure similar to that of tetracycline, but modified to inhibit MMP. Included are chemically modified tetracycline compounds, as described by U.S. Pat. No. 6,946,453, issued Sep. 20, 2005 (Ashley, et al.), U.S. Pat. No. 6,894,036, issued May 17, 2005 (Ashley, et al.), U.S. Pat. No. 6,638,922, issued Oct. 28, 2003 (Ashley, et al.), and U.S. Pat. No. 5,773,430, issued Jun. 30, 1998 (Simon, et al.).

As used herein, "matrix metalloprotease inhibitor", "MMP inhibitor", "inhibitor of matrix metalloprotease", or "inhibitor of MMP", means any compound that can prevent or slow the activity of a matrix metalloprotease or other zinc-containing proteinases. Examples of MMP inhibitors are, but not limited to, tissue inhibitors of metalloproteases (TIMPs), such as, but not limited to TIMP-1, TIMP-2, TIMP-3, and TIMP-4; analogs and homologs of tetracycline, such as, but not limited to, 4-dedimethylaminotetracycline and derivatives of 4-dedimethylaminotetracycline; DL-Thiorphan (N-[(RS)-2-Benzyl-3-mercaptopropanoyl]-glycine); TNF-α Protease Inhibitor-0 (N—(R)-[2-(Hydroxyaminocarbonyl)methyl]-4-methylpentanoyl-L-naphthylalanyl-L-alanine Amide); TNF-α Protease Inhibitor-1(N— (R)-[2-(Hydroxyaminocarbonyl)methyl]-4-methylpentanoyl-L-naphthylalanyl-L-alanine, 2-aminoethyl Amide); TNF-α Protease Inhibitor-2 (N—(R)-[2-(Hydroxyaminocarbonyl)methyl]-4-methylpentanoyl-L-t-butyl-alanyl-L-alanine, 2-aminoethyl Amide); 5-(5-(2-Chloro-5-trifluoromethyl-phenyl)-furan-2-ylmethylene)-4-oxo-2-thioxo-thiazolidin-3-yl)-acetic acid; doxycycline, N-[(2R)-2-(hydroxamidocarbonylmethyl)-4-methylpentanoyl]-L-tryptophan methylamide(ilomastat), minocycline, 3-(4-phenoxyphenylsulfonyl)propylthiirane, pyrimidine-2,4-dione, BAY12-9566, batimastat (BB-94), prinomastat (AG-3340), N-{1S-[4-(4-Chlorophenyl)piperazine-1-sulfonylmethyl]-2-methylpropyl}-N-hydroxyformamide, RO 31-9790, 3-(4-Phenoxyphenylsulfonyl)propylthiirane, 1,6-bis[N'-(p-chlorophenyl)-N5-biguanido]hexane, trocade, sodium 1-(12-hydroxy)octadecanyl sulfate, doxycycline, marimastat, minocycline (7-dimethylamino-6-dimethyl-6-deoxytetracycline), tetrapeptidylhydroxamic acid, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, N-Hydroxy-1,3-di-(4-methoxybenzenesulphonyl)-5,5-dimethyl-[1,3]-piperazine-2-carboxamide, N-{1S-[4-(4-Chlorophenyl)piperazine-1-sulfonylmethyl]-2-methylpropyl}-N-hydroxyformamide (U.S. Pat. No. 7,153,857, issued Dec. 26, 2006 (Finlay, et al.), triaryl-oxy-aryloxy-pyrimidine-2,4,6-trione, 4-biarylbutyric acid, 5-biarylpentanoic acid, Fenbufen, peptide MMPIs, hydroxamic acid, tricyclic butyric acid, biphenyl butyric acid, heterocyclic substituted phenyl butyric acid, sulfonamide, succinamide MMP inhibitor, sulfonated amino acid, neutralizing anti-MMP antibody, and their derivatives.

Examples of MMP-1 inhibitors are, but not limited to, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, FN-439 (MMP Inhibitor I, Cat. No. 444250 Calbiochem)-4-aminobenzoyl-Gly-Pro-D-Leu-D-Ala-NH—OH, N-Hydroxy-1,3-di-(4-methoxybenzenesulphonyl)-5,5-dimethyl-[1,3]-piperazine-2-carboxamide, MMP Inhibitor III, Cat. No. 444264 Calbiochem, (2-((Isopropoxy)-(1,1'-biphenyl-4-ylsulfonyl)-amino))-N-hydroxyacetamide, 4-(4-(Methanesulfonamido)phenoxy)phenylsulfonyl)methyloxirane Pyrimidine-4,6-dicarboxylic acid, bis-(4-fluoro-3-methyl-benzylamide), N-Hydroxy-1-(4-methoxyphenyl)sulfonyl-4-benzyloxycarbonylpiperazine-2-carboxamide, and N-Hydroxy-1-(4-methoxyphenyl)sulfonyl-4-(4-biphenylcarbonyl)piperazine-2-carboxamide.

Examples of MMP-2 inhibitors are, but not limited to, 1,6-bis[N'-(p-Chlorophenyl)-N5-biguanido]hexane, 2HCl, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, MMP Inhibitor III, Cat. No. 444264 Calbiochem, cis-9-Octadecenoyl-N-hydroxylamide, Oleoyl-N-hydroxylamide, N-[[(4,5-Dihydro-5-thioxo-1,3,4-thiadiazol-2-yl)amino]carbonyl]-L-phenylalanine Methyl Ester, a-[[[4,5-Dihydro-5-thioxo-1,3,4-thiadiazol-2-yl)amino]carbonyl]amino]-((2-pyridyl)piperazinyl)-(S)-benzenepropanamide, (2R)-2-[(4-Biphenylylsulfonyl)amino]-3-phenylpropionic Acid, (2R)-[(4-Biphenylylsulfonyl)amino]-N-hydroxy-3-phenylpropionamide, H-Cys1-Thr-Thr-His-Trp-Gly-Phe-Thr-Leu-Cys10-OH (cyclic: 1→10), SB-3CT (MMP-2/MMP-9 Inhibitor IV, Cat. No. 444274 Calbiochem), (S)-2-(4'-Bromo-biphenyl-4-sulfonylamino-3-methylbutyric acid), (2-((Isopropoxy)-(1,1'-biphenyl-4-ylsulfonyl)-amino))-N-hydroxyacetamide, (4-(4-(Methanesulfonamido)phenoxy)phenylsulfonyl)methyloxirane, Pyrimidine-4,6-dicarboxylic acid, bis-(4-fluoro-3-methyl-benzylamide), and α-[[[(4,5-Dihydro-5-thioxo-1,3,4-thiadiazol-2-yl)amino]carbonyl]amino]-N-(cyclohexylmethyl)-(S)-benzenepropanamide.

Examples of MMP-3 inhibitors are, but not limited to, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide; FN-439 (MMP Inhibitor I, Cat. No. 444250 Calbiochem)-4-aminobenzoyl-Gly-Pro-D-Leu-D-Ala-NH—OH, N-Hydroxy-1,3-di-(4-methoxybenzenesulphonyl)-5,5-dimethyl-[1,3]-piperazine-2-carboxamide, MMP Inhibitor III, Cat. No. 444264 Calbiochem, N-[[(4,5-Dihydro-5-thioxo-1,3,4-thiadiazol-2-yl)amino]carbonyl]-L-phenylalanine Methyl Ester, α-[[[4,5-Dihydro-5-thioxo-1,3,4-thiadiazol-2-yl)amino]carbonyl]amino]-((2-pyridyl)piperazinyl)-(S)-benzenepropanamide, Ac-RCGVPD-NH2, Stromelysin-1 Inhibitor, N-Isobutyl-N-(4-methoxyphenylsulfonyl)-glycylhydroxamic Acid, (S)-2-(4'-Bromo-biphenyl-4-sulfonylamino-3-methylbutyric acid), (4-(4-(Methanesulfonamido)phenoxy)phenylsulfonyl)methylthiirane, (2-((Isopropoxy)-(1,1'-biphenyl-4-ylsulfonyl)-amino))-N-hydroxyacetamide, Pyrimidine-4,6-dicarboxylic acid, bis-(4-fluoro-3-methyl-benzylamide), N-Hydroxy-1-(4-methoxyphenyl)sulfonyl-4-benzyloxycarbonylpiperazine-2-carboxamide, N-Hydroxy-1-(4-methoxyphenyl)sulfonyl-4-(4-biphenylcarbonyl)piperazine-2-carboxamide, N-Hydroxy-2(R)-{[(4-methoxyphenyl)sulfonyl]-[benzylamino]}-4-methylpentanamide, 3-[4-(4-cyanophenyl)phenoxy]propanohydroxamic Acid, 4-(4'-Biphenyl)-4-hydroxyimino-butyric Acid, 4-Dibenzofuran-2'-yl-4-hydroximino-butyric Acid, α-[[[(4,5-Dihydro-5-thioxo-1,3,4-thiadiazol-2-yl)amino]carbonyl]amino]-N-(cyclohexylmethyl)-(S)-benzenepropanamide, and N-[[(4,5-Dihydro-5-thioxo-1,3,4-thiadiazol-2-yl)amino]carbonyl]-L-phenylalanine.

Examples of MMP-7 inhibitors are, but not limited to, N-Hydroxy-1,3-di-(4-methoxybenzenesulphonyl)-5,5-dimethyl-[1,3]-piperazine-2-carboxamide, MMP Inhibitor III, Cat. No. 444264 Calbiochem, (2-((Isopropoxy)-(1,1'-biphenyl-4-ylsulfonyl)-amino))-N-hydroxyacetamide, (4-(4-(Methanesulfonamido)phenoxy)phenylsulfonyl)methyloxirane, Pyrimidine-4,6-dicarboxylic acid, bis-(4-fluoro-3-methyl-benzylamide), N-Hydroxy-1-(4-methoxyphenyl)sulfonyl-4-benzyloxycarbonylpiperazine-2-carboxamide, N-Hydroxy-1-(4-methoxyphenyl)sulfonyl-4-(4-biphenylcarbonyl)piperazine-2-carboxamide, and MMP-7 Antisense Oligonucleotide, Sodium Salt, Cat. No. 444266 (5'-GTATATGATACGATC-3')

Examples of MMP-8 inhibitors are, but not limited to, Pyrimidine-4,6-dicarboxylic acid, bis-(4-fluoro-3-methyl-benzylamide), (3S)-(−)-[2-(4-Methoxybenzenesulfonyl)-1,2,3,4-tetrahydroisoquinoline-3-hydroxamate], and (3R)-(+)-[2-(4-Methoxybenzenesulfonyl)-1,2,3,4-tetrahydroisoquinoline-3-hydroxamate].

Examples of MMP-9 inhibitors are, but not limited to, 1,6-bis[N'-(p-Chlorophenyl)-N-5-biguanido]hexane, 2HCl, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, FN-439 (MMP Inhibitor I, Cat. No. 444250 Calbiochem)-4-aminobenzoyl-Gly-Pro-D-Leu-D-Ala-NH—OH, N-Hydroxy-1,3-di-(4-methoxybenzenesulphonyl)-5,5-dimethyl-[1,3]-piperazine-2-carboxamide, (2R)-2-[(4-Biphenylylsulfonyl)amino]-3-phenylpropionic Acid, (2R)-[(4-Biphenylylsulfonyl)amino]-N-hydroxy-3-phenylpropionamide H-Cys1-Thr-Thr-His-Trp-Gly-Phe-Thr-Leu-Cys10-OH (cyclic: 1→10), SB-3CT (MMP-2/MMP-9 Inhibitor IV, Cat. No. 444274 Calbiochem), (4-(4-(Methanesulfonamido)phenoxy)phenylsulfonyl)methylthiirane, (2-((Isopropoxy)-(1,1'-biphenyl-4-ylsulfonyl)-amino))-N-hydroxyacetamide, Pyrimidine-4,6-dicarboxylic acid, bis-(4-fluoro-3-methyl-benzylamide), N-Hydroxy-1-(4-methoxyphenyl)sulfonyl-4-benzyloxycarbonylpiperazine-2-carboxamide, N-Hydroxy-1-(4-methoxyphenyl)sulfonyl-4-(4-biphenylcarbonyl)piperazine-2-carboxamide, and MMP-9 Inhibitor I, No. 444278, Calbiochem.

Examples of MMP-13 inhibitors are, but not limited to, CL-82198, Cat. No. 233105, Calbiochem, MMP Inhibitor III, Cat. No. 444264 Calbiochem, (S)-2-(4'-Bromo-biphenyl-4-sulfonylamino-3-methylbutyric acid), Pyrimidine-4,6-dicarboxylic acid, bis-(4-fluoro-3-methyl-benzylamide), N-Hydroxy-1-(4-methoxyphenyl)sulfonyl-4- benzyloxycarbonylpiperazine-2-carboxamide, N-Hydroxy-1-(4-methoxyphenyl)sulfonyl-4-(4-biphenylcarbonyl)piperazine-2-carboxamide.

The term "substituted" includes multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In embodiments of this invention, unsubstituted substituted aromatic rings include six-membered rings. In an embodiment the ring is substituted by a $C_1$-$C_{10}$ alkyl, alkenyl, or alkynyl, each of which may be linear or branched, and each of which may be substituted themselves with one or more amino groups. In an embodiment the substituted pyrrole groups of this invention are substituted by a $C_1$-$C_{10}$ alkyl, alkenyl, or alkynyl, each of which may be linear or branched, and each of which may be substituted themselves with one or more amino groups. In one embodiment the pyrrole group is substituted with an ethylamino group.

This invention will be better understood by reference to the Examples which follow, but those skilled in the art will readily appreciate that these specific examples are only illustrative of the invention as defined by the claims which follow thereafter.

It will be noted that the structures of certain compounds useful in this invention include asymmetric carbon atoms and thus occur as racemates and racemic mixtures, single enantiomers, diastereomeric mixtures and individual diastereomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention. Such isomers can often be obtained in substantially pure form by classical separation techniques and by stereochemically controlled synthesis procedures.

As set out above, certain compounds useful in this invention contain a basic functional group, such as an amino or alkylamino group, and are thus capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, e.g., Berge, et al. (1977) "Pharmaceutical Salts", *J. Pharm. Sci.* 66:1-19).

The term "pharmaceutically acceptable salts" as used herein also includes a quaternary ammonium salt.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Examples of materials which can serve as pharmaceutically acceptable carriers include: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for subcutaneous administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

Methods of preparing these formulations or compositions include the step of bringing into association a compound of the present invention with the carrier and, optionally, one or more accessory ingredients are well known in the art. In general, the formulations are prepared by uniformly and intimately bringing into association a compound of the present invention with liquid carriers, or finely divided solid carriers, or both, and then, if necessary, shaping the product.

Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of this invention suitable for parenteral administration comprise one or more compounds in combination with one or more pharmaceutically acceptable sterile isotonic aqueous or nonaqueous solutions, dispersions, suspensions, or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

The phrases "parenteral administration" and "administered parenterally", as used herein, mean modes of administration other than enteral and topical administration, usually by injection, and include, without limitation, intradiscal, intravenous, intramuscular, intraarterial, intrathecal, intracapsulaf, intraorbital, intracardiac, intradermal, intraperitoneal, transtracheal, subcutaneous, subcuticular, intraarticular, subcapsular, subarachnoid, intraspinal, and intrasternal injection and infusion.

The phrases "systemic administration", "administered systematically", "peripheral administration", and "administered peripherally", as used herein, mean the administration of a compound, drug or other material other than directly into the central nervous system, such that it enters the patient's system and, thus, is subject to metabolism and other like processes, for example, subcutaneous administration.

Actual dosage levels of the active ingredients in the pharmaceutical compositions used in the method of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health, and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

If general, a suitable daily does of a compound in the method of the invention will be that amount of the compound which is the lowest dose effective to produce a therapeutic effect. Such an effective dose will generally depend upon the factors described above.

If desired, the effective total dose of the active compound may be administered as two, three, four, five, six, or more sub-doses administered separately at appropriate intervals, optionally, in unit dosage forms.

Administration may be to multiple spinal segments. Where multiple spinal segments are involved, the treatment may be administered to all involved spinal segments in a single treatment session or at various times during a single day or a longer period of time. Administration to spinal segments may occur on multiple occasions or may be periodically performed, for example, once a month, semiannually, or once a year.

Lower back pain, with or without radiculopathy, continues to be a significant clinical symptom causing major disability in patients. Degeneration of the intervertebral discs has been implicated as one of the factors associated with lower back pain and is a probable prerequisite to disc herniations, which are associated most commonly with acute radicular syndromes. (See, for example, Kang, J. D., et al. "Kang I" (1996) Herniated Lumbar Intervertebral Discs Spontaneously Produce Matrix Metalloproteinases, Nitric Oxide, Interleukin-6, and Prostaglandin $E_2$," Spine, 21(3):271-277.

In the present invention disc degeneration is treated in mammalian subjects. Specifically, regenerative therapies comprising biological agents act to inhibit matrix metalloprotease (MMP) and treat disc degeneration. The regenerative therapy is delivered to the intervertebral disc and inhibits proteoglycan loss by interfering with the biochemical cascade that leads to disc degeneration.

Accordingly, the regenerative therapy comprises one or more MMP inhibitors in an amount effective to treat the subject. By treating the subject, the progress of disc degeneration is slowed or stopped.

MMP inhibitors reduce proteoglycan loss by interfering with the biochemical cascade that leads to disc degeneration.

Intervertebral disc is an avascular tissue populated by poorly characterized cells in an extensive extracellular matrix. The matrix of the central nucleus pulposus is rich in proteoglycans, whereas the annulus fibrosus is predominantly collagenous. With aging, the content of proteoglycans significantly decreases thereby contributing to disc degeneration. (See Kang I).

Matrix metalloproteases (MMPs), prostaglandin $E_2$ ($PGE_2$), and a variety of cytokines have been shown to play a role in the degeneration of articular cartilage. Nitric oxide (NO) is a novel mediator that is implicated in cartilage abnormalities. (See Kang I).

The clinical presentation of acute lumbar radiculopathy is most often attributed to a compressed lumbar nerve root by a herniated intervertebral disc. Some patients with large herniations have no radicular symptoms, and, in contrast, some patients with no evidence of disc herniations have severe radiculopathy. Direct mechanical compression of a nerve root and biochemical mediators of inflammation each play a role in disc degeneration and radicular pain. (See Kang I).

Biochemical mediators of inflammation and tissue degeneration play a role in intervertebral disc herniations and the pathophysiology of radiculopathy. (See Kang I).

Culture media from herniated lumbar discs show increased levels of matrix metalloprotease activity in comparison with control discs. Similarly, levels of nitric oxide, prostaglandin $E_2$, and interleukin-6 are significantly higher in herniated discs in comparison with control discs. Accordingly, herniated lumbar discs make spontaneously increased amounts of matrix metalloproteases, nitric oxide, prostaglandin $E_2$, and interleukin-6. These products are intimately involved in the biochemistry of disc degeneration and the pathophysiology of radiculopathy. (See Kang I).

Traditionally, disc degeneration has been considered to be largely a biochemical phenomenon. However, biochemical mechanisms are believed to play a much larger role than is generally appreciated. Articular cartilage provides a good example of how a cartilaginous tissue is vulnerable to the influences of biologic stimuli. For instance, in articular cartilage, interleukin-1 (IL-1) inhibits proteoglycan synthesis through a mechanism that, at least partly, involves the induction of nitric oxide (NO) synthesis. For example, Kang, J. D., et al., "Kang II" (1997) "Toward a Biochemical Understanding of Human Intervertebral Disc Degeneration and Herniation," SPINE 22(10):1065-1073.

Based on their roles in articular cartilage pathophysiology, NO and other biological agents are believed to be involved in the net loss of proteoglycans associated with disc degeneration.

Certain NOS inhibitors, for example L-NMMA, have been demonstrated to reduce the level of NO present, in vitro, in disc tissue obtained from human subjects. Kang I. Embodiments of the present invention seek to utilize various NOS inhibitors, for example GED, L-NAME, and L-NMMA to reduce NO production in vivo, within the discs of a patient suffering from disc degeneration. U.S. Ser. No. 11/505,161, filed Aug. 15, 2006 (Zahos).

Studies have shown that chronic lower back pain may be treated by direct intervertebral injection of biological agents. For example, Klein, R. G., et al. (2003) "Biochemical Injection Treatment for Discogenic Low Back Pain: a Pilot Study," The Spine Journal 3:220-226.

Based on the associations between MMP and disc degeneration, the present invention utilizes MMP inhibitors to interfere with the process of disc degeneration. The use of MMP inhibitors inhibits proteoglycan loss and/or reduces inflammation and neuropathic pain associated with disc degeneration. This is because MMP plays a regulatory role in the interaction between the biochemical agents produced by degenerated discs. Additionally, MMP production is a key modulator in proteoglycan loss and development of neuropathic pain.

Because disc degeneration is associated with the inflammatory cascade, it is contemplated that the inhibition of MMP would interfere with the progression of disc degeneration.

The pharmaceutical formulations of the present invention need not in themselves contain the entire amount of the agent needed to be effective; as such, effective amounts can be reached by administration of a single application or dose, or a plurality of applications or doses of such pharmaceutical formulations.

Pharmaceutical formulations of MMP inhibitors such as those listed above may be suitable for subcutaneous administration such as by injection directly into the affected discs via a needle and/or cannula. In addition to injection, other methods of currently preferred administration include infusion, irrigation, and other forms of known parenteral administration. For example, the treatment may be administered to the involved discs by infusion, for example using an infusion pump mechanism. For example, the treatment may be administered to the involved discs by irrigation, for example using arthroscopy.

The formulations may, where appropriate, be conveniently presented in discrete dosage units and may be prepared by any of the methods well known in the art of pharmacy. Such methods may include the steps of bringing into association the active compounds with liquid carriers or finely divided solid carriers or both, and then, if necessary, shaping the product into the desired formulation.

Formulations for parenteral administration include aqueous and non-aqueous sterile injection solutions which may contain anti-oxidants, buffers, bacteriostats, and solutes which render the formulation isotonic with the portion of the disc targeted for administration. The formulations may be presented in unit-dose or multi-dose containers, for example sealed ampoules and vials, and may be stored in a freeze-dried (lyophilized) condition requiring only the addition of the sterile liquid carrier, for example, saline water-for-injection, immediately prior to use.

According to one embodiment of the present invention, the therapeutic agents could be delivered by percutaneous intradiscal delivery in a biopolymer substrate. The biopolymer substrate may comprise, for example, hyaluronic acid or a pharmaceutically acceptable salt or ester thereof. The therapeutic could be delivered to multiple spinal segments, and in sequential applications, with the goal of ameliorating proteoglycan loss and concomitant discogenic pain.

The therapeutic agent may be combined with the biopolymer substrate such that the therapeutic agent comprises preferably 0.1% to 5% of the combined substance, and more preferably 0.1% to 1.0% of the combined substance.

Alternatively, the therapeutic agents may be administered in conjunction with a surgical procedure, for example, during a surgical procedure such as laminectomy or microdiscectomy. The therapeutic agents may be administered directly to exposed discs.

According to one embodiment of the present invention, the therapeutic agents may be administered during a single application. Alternatively, the therapeutic agents may be administered multiple times over a period of between one and ten days. Treatment may occur once, periodically, or as needed.

Additional references relating to this invention include the following: *Inflammatory Mediators as Potential Therapeutic Targets in the Spine*, Sally Roberts, et al., Current Drug Targets—Inflammation & Allergy, 2005, 4, 257-266; *Possible Pathogenesis of Painful Intervertebral Disc Degeneration*, Baogan Peng, et al., SPINE vol. 31, no. 5, pp 560-566, 2006; *Human Nucleus Pulposis Can Respond to a Pro-inflammatory Stimulus*. J. G. Burke, et al., SPINE vol. 28, no. 24, pp 2685-2693, 2003; *Possible Mechanism of Painful Radiculopathy in Lumbar Disc Herniation*, Mamoru Kawakami, et al., Clinical Orthopaedics and Related Research, no. 351, pp 241-251, 1998; *Anti-Apoptotic Effects of Caspase Inhibitors on Rat Intervertebral Disc Cells*, Jong-Beom Park, et al., Journal of Bone and Joint Surgery, 2006; *The Potential of Gene Therapy for the Treatment of Disc Degeneration*, S. Tim Yoon, Orthop Clin N Am 35 pp 95-100, 2004; *Gene Therapy Application for Intervertebral Disc Degeneration*, Corey J. Wallach et al., SPINE vol. 28, no. 15S, pp S93-S98, 2003; *Gene Therapy to Prevent or Treat Disc Degeneration: Is This the Future?*, Eric A. Levicoff et al., SpineLine March/April 2005 pp 10-16; *Adenovirus-Mediated Gene Transfer to Nucleus Pulposus Cells*, Kotaro Nishida, et al., SPINE vol. 23, no. 22, pp 2437-2443, 1998; *Emerging Techniques for Treatment of Degenerative Lumbar Disc Disease*, Howard An et al., SPINE vol. 28, no. 15S, pp S24-S25; *Biologic Treat-* ment for Intervertebral Disc Degeneration, Frank Phillips et al., SPINE vol. 28, no. 15S, p S99, 2003; *Biological Repair of Intervertebral Disc*. Howard S. An, et al., SPINE vol. 28, no. 15S, pp S86-S92, 2003; *Cell Therapy for Disc Degeneration-potentials and pitfalls*, Helena Brisby et al. Orthop Clin N Am 35 (2004) 85-93; *Intervertebral Disc Cell Therapy for Regeneration: Mesenchymal Stem Cell Implantation in Rat Intervertebral Discs*, Gwen Crevensten et al., Annals of Biomedical Engineering vol. 32, no. 3, March 2004 pp. 430-434; *Safety Assessment of Intradiscal Gene Transfer: A pilot study*, Corey J. Wallach et al., The Spine Journal 6 (2006) 107-112; *Sequiteroene Lactones Specifically Inhibit Activation of NF-κB by Preventing the Degradation of kB-a and IκB-P*, Steffen P. Hehner et al., The Journal of Biological Chemistry, vol. 273, no. 3, issue of January 16, pp 1288-1297, 1998.

The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

EXPERIMENTAL DETAILS

Materials and Methods

Example 1

To follow the process of disc degeneration caused by annular injury, radiographic and histological assessment is performed using the annulus needle puncture procedure using 18G needles, as reported by Matsuda, et al., "A Novel Rabbit Model of Mild, Reproducible Disc Degeneration by an Annulus Needle Puncture: Correlation Between the Degree of Disc Injury and Radiological and Histological Appearances of Disc Degeneration," SPINE 30(1):5-14 (2004). See also Sobajima, S, et al., "A Slowly Progressive and Reproducible Animal Model of Intervertebral Disc Degeneration Characterized by MRI, X-Ray, and Histology," SPINE 30(1):15-24 (2004).

Animal Model and Experimental Setup

Needle stabs are performed to create disc degeneration in the rabbit model. Ten rabbits are used and each animal serves as its own control. The experimental design is summarized in Table 1.

TABLE 1

Experimental Design for Rabbit Study

| Disc Location | Treatment | Duration |
|---|---|---|
| T12-L1 | None | 8 wks |
| L1-L2 | Needle stabbed Inject hydrogel | 8 wks |
| L2-L3 | Needle stabbed Inject hydrogel/CMT-3 #1 | 8 wks |
| L3-L4 | Needle stabbed Inject hydrogel/CMT-3 #2 | 8 wks |
| L4-L5 | Needle stabbed PBS | 8 wks |

Lateral plain radiographs are obtained to determine baseline values for intervertebral disc (IVD) heights before any intervention. Rabbits under general anesthesia are put into a lateral prone position, and the anterior surfaces of consecutive lumbar IVDs (T12-L1, L1-L2, L2-L3, L3-L4, L4-L5, and L5-L6) are exposed by a posterolateral retroperitoneal approach. The areas punctured (1-2 mm diameter) are exposed upon determining the disc levels after palpitation. Four of the five exposed discs are punctured by an 18 gauge needle and the depth of the needle stab is controlled to exactly 5 mm with a custom-built stopper-bumper. The needle is inserted at the center of the disc level through the annulus fibrosus into the nucleus pulposus and held for 5 seconds following the described protocol. MRI images (sagittal plane) of the spine are captured. MRI imaging software algorithms allow for user-adjusted placement of the sagittal midline and a proper axial image through the center of the disc space. Upon completing the procedure, the rabbits are returned to their colonies for 2 weeks and allowed to develop the condition comparable to disc degeneration as described previously.

Following the protocol described above, the rabbits are anesthetized, a lateral plain radiograph is taken, and undergo a second procedure and a spine MRI image is captured; 100 μL of two doses of the CMT-3/hydrogel formulation is injected into the spinal discs previously stabbed with needles, as is hydrogel alone. Physiological phosphate buffered saline (PBS) is used as the vehicle for preparing the hydrogels. For the controls, a comparable volume of PBS is injected. Soon after the injection, MRI images are captured and the animals are returned to their colonies.

Efficacy Assessment (MRI Image Evaluation and Histology Analyses)

Lateral plain radiograph and MRI images of the spines are captured at 2 and 4 weeks and at the conclusion of the study (i.e., 8 weeks). Thereafter, the animals are sacrificed and their spines recovered and processed for histology analyses. The algorithms previously derived by Masuda, et al. are utilized to evaluate the outcomes (both images and histological specimens).

Image Evaluation

Both radiographic and MRI images are evaluated by an observer that is blinded to the experimental protocol using modified Thompson classification based on changes in the degree and area of signal intensity from Grade 1 to 4, to establish a Disc Height Index (% DHI).

| 1 = | normal |
|---|---|
| 2 = | minimal decrease of signal intensity but obvious narrowing of high signal area |
| 3 = | moderate decrease of signal intensity |
| 4 = | severe decrease of signal intensity |

Specimen Preparation and Evaluation

Upon finishing the final radiographic procedure, the animals are sacrificed and discs are harvested for histological assessments. The tissues are first fixed in 10% neutral buffered formalin (with 10% added cetylpyridinium chloride), followed by decalcification in Cal-Ex II™ Fixative/Decalcifier (Fisher Scientific, Pittsburgh, Pa.); then, paraffin-embedded, and 6 μm thick sections are produced. The sections are H&E stained for cellular constituents and Safranin-O stained for proteoglycans. Rosenberg, L. (1971) "Chemical basis for the histological use of safranin O in the study of articular cartilage," J Bone Joint Surg Am, 53:69-82. Picrosirius staining is performed to assess collagen fiber orientation via polarizing microscopy. Junqueira L. C., et al. (1979) "Picrosirius staining plus polarization microscopy, a specific method for collagen detection in tissue sections." Histochem J, 11:447-55. The above-mentioned grading scale established by Masuda, et al. is employed to assess the stages of disc degeneration. Kang J. D., et al. (1997) "Toward a biochemical understanding of human intervertebral disc degeneration and herniation. Contributions of nitric oxide, interleukins, prostaglandin E2, and matrix metalloproteinases," Spine 22(10): 1065-1073.

Example 2

[Reproducing the Article Fingleton, B., "CMT-3 CollaGenex," Current Opinion in Investigational Drugs 4(12): 1460-1467 (2003).]

CMT-3 is an orally active matrix metalloprotease inhibitor, and one of a series of inhibitors of multiple proteases and cytokines, under development by CollaGenex. The compound is currently undergoing phase II trials for the potential treatment of cancer, in particular metastatic cancer and HIV-related Kaposi's sarcoma.

Introduction

CMT-3 (chemically modified tetracycline/COL-3/Metastat) is one of a series of chemically modified tetracyclines (CMTs) produced as inhibitors of matrix metalloproteases (MMPs).

These compounds are under development for their potential in cancer therapy [190720]. The chemical modification of the tetracycline antibiotics ensures that they no longer possess any antimicrobial activity. Like the antibacterial compounds tetracycline, doxycycline and minocycline, CMTs inhibit both production and activity of various members of the MMP family of enzymes. MMPs are a class of neutral zinc-dependent endopeptidases with the ability to degrade proteinaceous components of the extracellular matrix, as well as other substrates [439895]. They are particularly associated with tumor angiogenesis, invasion and metastasis [428456] and arthritic diseases [495636], although they have also been shown to play roles in many other pathologies including atherosclerosis [495640], diabetes [376241], chronic obstructive pulmonary disease [495642], psoriasis [495646] and neurological disorders [495649].

A number of MMP inhibitors, the best known being British Biotech plc's marimastat, have been developed by various pharmaceutical companies [173287]; however, none of these, including marimastat, have successfully completed clinical trials [493831]. In fact, the only FDA-approved drug marketed for its MMP-inhibiting activity is CollaGenex's Periostat, a low-dose doxycycline for the treatment of periodontal disease [305939], [384958].

CMT-3 falls under CollaGenex's IMPACS (inhibitors of multiple proteases and cytokines) patented technology as it appears to have a dual mechanism of action, both inhibiting proteases and downregulating various inflammatory mediators that have been implicated in tumor progression [367204]. Although the primary drug targets are MMPs, CMT-3 has also been reported to inhibit other neutral proteases of the serine protease family [350261]. Additionally, the inflammatory molecules inducible nitric oxide synthase (iNOS) and cyclooxygenase-2 (COX-2) are also reported as targets [350249], [350270]. Although CMT-3 has been demonstrated to augment COX-2 expression, it modifies the COX-2 protein rendering it inactive, thus leading to a decrease in prostaglandin $E_2$ (PGE$_2$) production [350249].

CMT-3 is being explored both preclinically and clinically as an anticancer agent [350324]. Other therapeutic areas are less well developed; CollaGenex was to develop CMT-3 for acute lung injury and was considering developing it for several inflammatory diseases [350244], [467178].

Synthesis and SAR

In the initial synthesis, the basic tetracycline four-ring structure was modified to remove the dimethylamino group from the C(4)-position on the A ring using a method based on previously published techniques [236452]. This eliminated the antimicrobial activity of the tetracycline but maintained the MMP inhibitory activity; the antibiotic and anticollagenase activity reside in different parts of the molecule. The MMP inhibitory activity might depend on the ability of CMT-3 to bind metal ions using the carbonyl and hydroxyl groups, which were unaffected by the chemical modification. The metal ions are required by MMPs to maintain their conformation and hydrolytic activity. Further changes in the side chains led to a series of ten CMTs. CMT-3, also known as COL-3, is the simplest of these structures with no side chains at the C(4)- or C(6)-positions. The various analogs in this series differ in their MMP specificity, potency and oral bioavailability.

Other members of this series, as well as newer analogs, are in preclinical development by CollaGenex for a variety of pathologies: CMT-8 (Nephrostat) is being evaluated for diabetic nephropathy, CMT-6 (Dermastat) is under investigation for wound repair, and Arthrostat, Osteostat and Rheumastat are being investigated for osteoarthritis, osteoporosis and rheumatoid arthritis, respectively [181233], [350244]. Of the seven CMTs evaluated by Seftor and colleagues at The University of Iowa, CMT-3 was the most effective MMP-2 inhibitor and the second most potent MMP-9 inhibitor, as determined by zymography. It was also the most active, with an activity comparable to doxycycline at inhibiting the in vitro invasive ability of a human melanoma cell line, as well as rheumatoid arthritis synoviocytes [494695]. This specificity could also be related to the binding of CMT-3 to $Ca^{2+}$ and $Zn^{2+}$ [439895], [494695].

Loss of the antibiotic activity of the compounds prevented the use of the standard bioassay to quantitate CMTs, and necessitated the development of new methods for detecting CMT-3 in human plasma. One method based on high-performance liquid chromatography with mass spectrometry detection has been used to determine levels of the drug in plasma samples from patients in clinical trials [494714].

Preclinical Development

Early literature referred to the anticollagenolytic activity of CMTs [501081]. This is a somewhat confusing description as the classical type I collagenase, MMP-1, is not a target of these drugs; however, other collagenases, such as MMP-8 and MMP-13, are targets [350269]. CMTs exhibit potent antigelatinolytic activity, the enzymes involved being gelatinases A and B, also known as MMP-2 and -9. MMP inhibitors have classically been divided into broad spectrum and those with selective inhibition profiles. CMT-3 is a selective inhibitor with its principal targets being gelatinases. It has a dissociation binding constant ($K_i$) value for MMP-2 of 74 µM and a $K_i'$ (the dissociation equilibrium constant) value of 148 µM for MMP-2, indicating both competitive and non-competitive inhibition [350268]. This is similar to the results seen with doxycycline, which showed a $K_i'$ value for MMP-2 of 144 µM.

In vitro testing of CMT-3 and doxycycline demonstrated that both drugs were significantly cytotoxic to a panel of prostate cancer cell lines when tested using MTT assays. Further analysis, however, showed that CMT-3 induced apoptosis in these cells in a concentration-dependent manner and within 4 h of exposure, whereas doxycycline did not induce apoptosis [494720]. A specific effect on angiogenesis was examined by assaying microtubule formation by human umbilical vein endothelial cells (HUVECs) stimulated with angiogenic factors in vitro [494725]. Both doxycycline and CMT-3 inhibited microtubule formation while CMT-3 also inhibited HUVEC proliferation. Vascular mimicry is a recently described phenomenon whereby certain aggressive tumors can form a blood supply in the absence of endothelial cells. CMT-3 inhibited this mechanism in metastatic melanoma cells in vitro [486824].

A mechanism by which doxycycline and CMTs have been shown to exert anti-inflammatory effects in vitro is through the inhibition of iNOS with consequent downregulation of nitric oxide production [350271]. CMT-3 increases iNOS mRNA degradation. This may allow the drug to be used in the treatment of diseases mediated by excessive nitric oxide production [350270]. In addition, CMT-3 has been shown to inhibit COX-2 enzyme activity in vitro [350249].

Initial testing in vivo indicated that CMT-3 significantly reduced the number of lung foci in an experimental metastasis assay in severe combined immunodeficiency (SCID) mice when administered orally at 40 mg/kg. However, a higher dose (100 mg/kg) did not significantly impact metastatic invasion when compared with control animals. This confounding result is suggested to be due to the poor solubility of CMT-3, which at high concentration could cause the drug to precipitate out of the system and, therefore, lead to an overall lower plasma concentration at the higher dose relative to the lower, non-precipitating dose [494695].

CMT-3 and doxycycline were examined in prostate cancer models in vitro and in vivo. CMT-3 increased apoptosis and necrosis as well as cell-cycle arrest when added to prostate cell lines in vitro. In the Dunning MatLyLu rat prostate tumor model, decreases in tumor growth and spontaneous lung metastases were observed after daily gavage at 40 mg/kg for 7 days. CMT-3 caused tumor growth delays of between 27 and 35% compared with control, while CMT-3- and doxycycline-treated animals had instances of lung metastases of 28.9±15.4 and 43.6±18.8 tumors/animal, respectively, compared with 59.5±13.9 tumors/animal in controls. The response to CMT-3 could be extended to effects on primary tumor incidence (a decrease of 55±9%), growth (a delay of 27±9.3%) and reduction in metastases (by 58±8%) by pre-dosing the rats for 7 days [486833].

Metabolism and Pharmacokinetics

CMT-3 has poor water solubility (~0.01 mg/ml), but is readily soluble in organic solvents. Its lipophilicity means that it is easily taken up by cells. Stability and solubility are inversely related, with maximum stability seen at pH<4. For in vivo preclinical and clinical studies, CMT-3 was formulated as a capsule, or a suspension for oral dosing, as it is orally bioavailable and well absorbed [494714].

An irregular absorption profile with a double or plateau concentration was reported in a study of rats administered a single oral dose of a CMT-3 suspension. The half-life was approximately 6 h. variability in the dissolution rate of the solid drug in gastrointestinal fluids was found to be responsible for the irregular profile and was influenced by drug particle size, presence of food and endogenous bile [494736].

A pharmacokinetic study in rats and monkeys demonstrated terminal half-lives of 7 h in rats and from 28 to 1426 h in monkeys. Bioavailability ranged from 9 to 56% in both species [501235].

Results from two different dose-escalation studies in humans demonstrated that CMT-3 plasma levels increased with doses up to 50 mg/m$^2$/day; above this dose, the steady-state concentration reached a plateau indicating a saturation of absorption [390776], [390777]. All doses tested resulted in steady-state plasma concentrations higher than levels required for efficacy in preclinical models. The clearance rate was slow, with a total apparent clearance of 0.0098±0.0058 l/h/kg as calculated in a pharmacokinetic study conducted with 35 patients with refractory metastatic cancers [390777]. Computer analysis indicated that the pharmacokinetic data best fit a one-compartment model with first-order absorption and elimination. In this study, the median half-life was approximately 56.1 h, which is 2- to 11-fold longer than for other tetracycline derivatives. The median apparent total clearance and pseudo-steady-state apparent volume of distribution were 0.01 l/h/kg and 0.64 l/kg, respectively [407127]. A study in 18 patients with AIDS-associated Kaposi's sarcoma (KS) gave a median half-life of 39.3 h; however, in this case pharmacokinetic sampling lasted only 24 h [486836].

In a phase I study of 11 patients administered 36 or 50 mg/m$^2$ of CMT-3, the half-life measured in five patients was between 61 and 96 h after a single-dose administration, and from 37 to 87 h after multiple dosing. The steady-state concentrations for five of the patients ranged from 2540 to 11,040 ng/ml [367204], [501235].

Toxicity

In a preclinical dose-finding study performed in rats and monkeys, animals were dosed with CMT-3 in different schedules up to 300 mg/kg/day [249339]. Mortalities occurred in rats at 200 or 300 mg/kg/day depending on the schedule. At a dose of 100 mg/kg/day, histopathological lesions were observed in the small intestine and thymus. In monkeys, doses of 100 mg/kg/day on any dosing schedule resulted in mortalities after three to five doses. Again, histopathological lesions were evident in the small intestine. The gastrointestinal toxicities, which were dose-limiting in both species, occurred when plasma levels of CMT-3 reached 15 mg/ml or greater, and were claimed to be at a much higher level than that needed for MMP inhibition [249339].

In 142 animals administered CMT-3 as daily gavage (40 mg/kg) for 7 days, no adverse effects or weight loss were noted. [486833]. No other animal studies reported any systemic toxicities. The related molecule doxycycline has been reported to moderately inhibit immune responses [494740] and to have a hepatotoxic effect in mice; however, it is still regarded as a compound with low toxicity [494744].

Clinical Development

Phase I

CMT-3 entered phase I trials in cancer as part of a collaboration between CollaGenex and the NCI [252107]. Two trials were performed in groups of patients with diverse cancers [390776], [407127], and a third specifically targeted patients with AIDS-associated KS in a trial conducted under the auspices of the AIDS malignancy consortium [442743]. KS is a malignancy with a strong angiogenic component and is, therefore, a suitable target for an agent with anti-angiogenic activity [428317].

The diverse cancer trials began with an accelerated titration design for a rapid determination of the maximum tolerated dose (MTD) [390776], [407127]. Since grade 2 phototoxicity was observed at the first dose level, the trials were converted to a standard three-to-six-patient protocol per initial dose with subsequent dose levels determined by the Fibonacci sequence. In both of these trials, four dose levels were tested: 36, 50, 70 and 98 mg/m$^2$/day. At the highest dose, all 18 patients developed sunburn (due to photosensitivity) despite prophylactic measures, an event that was dose-limiting. The trial in KS patients used three dose levels: 25, 50 and 70 mg/m$^2$/day [486836]. CMT-3 was reasonably well tolerated at doses up to 70 mg/m$^2$/day, with photosensitivity again being the principal toxicity observed. Doses of >50 mg/m$^2$/day were not tolerated. Decreases in plasma concentrations of drug targets MMP-2 and MMP-9 were evident in 61 and 37% of evaluable patients, respectively. There was a significant difference in MMP-2 levels between responding (decrease of 56 ng/ml from baseline) and non-responding (increase of 300 ng/ml from baseline) patients. In all three trials, preliminary analysis of biological correlates, principally plasma levels of MMP-2 or MMP-9, indicated effects on expression of these targets [407127], [409854], [486836].

In a study of 35 patients with refractory metastatic cancers administered CMT-3 from 36 mg/m$^2$/day, there was an apparent relationship between MMP-2 levels and cumulative dose. The MTD was 98 mg/m$^2$/day [407127]. Overall, however, there was no significant change between pre- and post-treatment levels of either MMP-2 or MMP-9 in these patients. Disease-stabilization was observed in three out of seven (43%) patients with tumors of non-epithelial origin included as part of the cohort [407127], suggesting that similar tumors would be a reasonable group for further testing.

For the KS trial, 18 patients were recruited, 17 of whom had recurrent disease following previous chemotherapy. Of these patients, 14 were also undergoing a highly active antiretroviral therapy (HAART) regimen while on the study. This trial reported an overall response rate of 44%, consisting of one complete and seven partial responses. The median time to response was 4 weeks with a median duration of >25 weeks. The changes in the MMP-2 serum levels after treatment were different between responders and non-responders. MMP-2 levels in responders decreased by 56 ng/ml, whereas in non-responders, levels increased by 300 ng/ml. Levels of the angiogenic factor vascular endothelial growth factor showed a similar trend, but the changes did not reach statistical significance. These data have been used as support for continuing the clinical development of CMT-3 in KS patients [486836].

Another National Cancer Institute (NCD-sponsored phase I/II trial of CMT-3 in patients with progressive or recurrent brain tumors has stopped recruiting patients. This trial will examine dosing, toxicity and pharmacokinetic parameters for oral CMT-3 alone and in combination with anticonvulsants metabolized by cytochrome P450 [494756].

Phase II

No data have yet been reported for phase II testing of CMT-3; however, enrollment into a trial in 75 patients with AIDS-related KS has been completed, and results are anticipated by December 2003. This is a multicenter, open-label study in which patients will receive one of two different doses for 6 months with at least a 1-month follow-up [483919].

A double-blinded, placebo-controlled, phase II trial has also been initiated to evaluate the safety and efficacy of CMT-3 in treating patients with rosacea. This study will enroll 30 patients and the primary endpoint will include changes in facial lesions and redness [498815].

Side Effects and Contraindications

Tetracyclines are known to cause photosensitivity [505156], [505157] and in all human trials of CMT-3 to date, the principal and dose-limiting toxicity was photosensitivity. This dose-related toxicity manifested as erythema, with pain and blisters at higher grades. Sun-block usage was mandatory at dose levels of 50 mg/m$^2$/day; however, over 50% of patients still experienced some phototoxicity [407127]. The other most frequently reported adverse events were fatigue and anemia, although these were not related to dose. While aplastic, megaloblastic and hemolytic anemias have previously been reported to be associated with tetracycline-related drugs, the trial in 35 patients with refractory metastatic cancers revealed a novel association with three cases of reversible sideroblastic anemia [494759]. The three patients all demonstrated resolution of the anemia after withdrawal from CMT-3, although one patient resumed treatment and again developed sideroblastic anemia. The same trial also produced three cases of drug-induced lupus with erythemas, fever and a positive antinuclear antibody titer [494762]. Two of the three patients also showed antihistone antibodies and arthralgia. In these two cases, withdrawal from CMT-3 resulted in resolution of the lupus symptoms within 2 weeks, although serology markers remained abnormal. The third patient, a 63-year-old man with metastatic prostate cancer, developed systemic manifestations of lupus, including pulmonary infiltrates. This patient continued to have recurrences of symptoms over one year after discontinuing CMT-3 [494762].

Other reported adverse events include headache, nausea or vomiting, anorexia, constipation, dizziness, neurotoxicities and elevated liver-function test results [407127]. This is a similar spectrum of side effects as that reported for doxycycline in a phase I trial of patients with advanced cancers [494782]. Interestingly, there were no reports of the musculoskeletal side effects that have plagued clinical trials of other MMP inhibitors [494768], an outcome most likely related to the selective inhibitory profile of CMT-3.

Patent Commentary

WO-09831224, covering a method of inhibiting the growth and metastasis of sarcoma, carcinoma, adenocarcinoma and melanoma by the administration of CMTs, including CMT-3, was awarded to SUNY in July 1998. By November 1999, SUNY also held a number of other patents covering CMT-3, including its use in cancer invasion (WO-09949871), inflammatory diseases (WO-09930720), lung injury (U.S. Pat. No. 5,977,091) and several other diseases (U.S. Pat. No. 5,773,430). By February 1999, CollaGenex had been awarded U.S. Pat. No. 5,837,696, claiming the use of CMT-3 for the inhibition of cancer metastasis [314866]. In January 2003, CollaGenex was issued U.S. Pat. No. 6,506,740 covering 4-dedimethylaminotetracycline derivatives and their use for a wide variety of diseases involving, among other things, the destruction of the body's connective tissues [481027].

Current Opinion

The clinical history of MMP inhibitors has been extremely disappointing. Several drugs have completed phase III trials in various cancers, yet none have successfully reached the primary endpoint of improved patient survival [494768]. In some cases, dose-limiting side effects have necessitated dose-lowering or drug holidays, resulting in treatment regimens that may not have maintained effective therapeutic levels of the drugs. One significant problem with these drugs has been the lack of an assay for in vivo biological activity of the agents. CMT-3 differs from previous MMP inhibitors in a number of significant ways: (i) it is predominantly a gelatinase inhibitor with limited effects on fibrillar collagenases; (ii) no musculoskeletal effects have been observed in either preclinical or clinical testing to date; (iii) the compound has effects on other enzymes (e.g., COX-2 and iNOS) that may enhance its therapeutic potential; and (iv) it inhibits both production and activity of MMPs, allowing a reasonably straightforward measure of functionality in vivo. It is this last attribute of CMT-3 that makes it a particularly attractive MMP inhibitor from the point of view of clinical testing. Early indications from phase I trials, particularly in KS patients, are that CMT-3 treatment can reduce MMP levels and that this correlates with clinical response. Focusing on KS was a wise decision given the lack of efficacy of previous MMP inhibitors in other, high-grade, aggressive, solid tumors in which many molecular pathways contribute to tumor progression. As KS is a prominently angiogenic malignancy, it seems reasonable that an agent with demonstrated anti-angiogenic activity will have an impact. Based on results from other molecularly targeted agents in cancer, it seems likely that true efficacy in most tumor types will only be apparent when CMT-3 is used in combination, or in the adjuvant setting. As a word of caution, other MMP inhibitors also looked worthy of continued development after phase I and II trials, so it is not until a phase III trial is completed that we can determine whether CMT-3 is truly distinct from previous MMP inhibitors.

ASSOCIATED PATENT

Title Method of treating cancer and metastasis using metalloproteinase-inhibitory tetracyclines.
Assignee The Research Foundation of State University of New York/University of Miami
Publication WO-09S31224 23 Jul. 1998
Priority US-00783655 15 Jan. 1997
Inventors Golub L M, McNamara T F, Ramamurthy N S, Lee H-M, Simon S, Lokeshwar B L, Selzer M G, Block N L

ASSOCIATED REFERENCES

173287 Batimastat clinical programme revised. British Biotech plc PRESS RELEASE 1995 Feb. 17
181233 CollaGenex: Therapies for periodontal diseases: Corporate Profile. CollaGenex Inc COMPANY BROCHURE 1995
190720 CollaGenex Inc executes agreement for exclusive license to collagenase-inhibiting technology from State University of New York at Stony Brook. CollaGenex Inc PRESS RELEASE 1994 Nov. 30
228097 CollaGenex and Boehringer Mannheim sign cancer research cooperation agreement. CollaGenex Pharmaceuticals Inc PRESS RELEASE 1996 Dec. 11
236452 A non-antibacterial chemically-modified tetracycline inhibits mammalian collagenase activity. Golub L M, McNamara T F, D'Angelo G, Greenwald R A, Ramamurthy N S J DENT RES 1987 66 8 1310-1314
249339 Preclinical dose-ranging studies of COL-3 (NSC-683551) in rats and monkeys. Rodman L, Farnell D, Tomaszewski J, Smith A, Oage-J PROC ANNU MEETA-MASSOC CANCER RES 1997 38 Abs 4021
252107 National Cancer Institute extends collaboration with CollaGenex Pharmaceuticals Inc. CollaGenex Pharmaceutical Inc PRESS RELEASE 1997 Jul. 1
271418 NCI files IND for first CollaGenex cancer drug. CollaGenex Pharmaceutical Inc PRESS RELEASE 1997 Dec. 5
305939 CollaGenex launches Periostat first-of-its-kind medication In capsule form for adult periodontitis. CollaGensx Inc PRESS RELEASE 1998 Nov. 18
314866 CollaGenex reports findings from Metastat clinical study. CollaGenex Pharmaceuticals Inc PRESS RELEASE 1999 Feb. 11
350244 Drug development pipeline: COL-3, COL-8, Dermastat, Arthrostat, Osteostat and Rheumastat. CollaGenex Pharmaceuticals Inc COMPANY COMMUNICATION 1999 Dec. 13
350249 A novel mechanism of action of chemically modified tetracyclines: Inhibition of COX-2-mediated prostaglandin $E_2$ production. Patel R N, Attur M G, Dave M N, Patel I V, Stuchin S A, Abramson S B, Amin A R J IMMUNOL 1999 163 6 3459-3467
350261 Matrix metalloproteinase inhibitor prevents acute lung injury after cardiopulmonary bypass. Carney D E, Lutz C J, Picone A L, Gatto L A, Ramamurthy N S, Golub L M, Simon 3R, Searles B, Paskanik A, Snyder K, Fmck C CIRCULATION 1999 100 4 400-406
350268 Chemically modified tetracyclines inhibit human melanoma cell invasion and metastasis. Seftor R E, Saftor E A, De Larco J E, Kleiner D E, Leferson J, Stetler Stevenson W G, McNamara T F, Golub L M, Hendrix M J CLIN EXP METASTASIS 1998 16 3 217-225
350259 In vitro sensitivity of the three mammalian collagenases to tetracycline inhibition: Relationship to bone and cartilage degradation. Greenwald; R A, Gclub L M; Ramamurthy N S, Chowdhury M, Moak S A, Sorsa J BONE 1998 22 1 33-38
350270 Post-transcriptional regulation of inducible nitric oxide synthase mRNA in murine macrophages by doxycycline and chemically modified tetracyclines. Amin A R, Patel R N, Thakker G D, Lowenstein C J, Attur M G, Abramson S B FEBS LETT 1997 410 2-3 259-264
350271 Chemically modified tetracyclines inhibit inducible nitric oxide synthase expression and nitric oxide production in cultured rat mesangial ceils. Trachtman H, Futterweit S, Greenwald R, Moak S, Singhal P, Franki. N, Amin A R BIOCHEM BIOPHYS RES COMMUN 1996 229 1 243-248
350324 CollaGenex Pharmaceuticals: Research and technologies. CollaGenex Pharmaceuticals inc COMPANY WORLD WIDE WEB SITE 1999 Dec. 13
367204 Angiogenesis inhibitor shows early promise in treatment of Kaposi's sarcoma. Data presented at international AIDS Malignancy Conference demonstrate general tolerability, anti-tumor effect with Col-3. CollaGenex Pharmaceuticals Inc PRESS RELEASE 2000 May 18
376241 MMP-mediated events in diabetes. Ryan M E, Ramamurthy N S, Sorsa T. Golub L M ANN NY ACAD SCI 1999 873 311-334
384958 CollaGenex Pharmaceuticals announces availability of Periostat in United Kingdom. CollaGenex Pharmaceuticals Inc PRESS RELEASE 2000 Oct. 5
386137 CollaGenex Pharmaceuticals Inc awarded STTR grant to study acute lung injury. CollaGenex Pharmaceuticals inc PRESS RELEASE 2000 Oct. 18
390776 A phase I and pharmacokinetic (PK) study of Col-3, an oral tetracycline analog and selective matrix metalloproteinase (MMP) inhibitor. Rowinsky E, Eckhardt S, Rizzo J, Kuhn J NCI EORTC SYMP NEW DRUGS CANCER THER 2000 11 Abs 292
390777 Pharmacokinetics {PK) of COL-3, a matrix metalloproteinase (MMP) inhibitor. Rudek M, Dyer V, Dahut W, Pluda J, Reed E, Figg W NCI EORTC SYMP NEW DRUGS CANCER THER 2000 11 Abs 293
407127 Phase I clinical trial of oral COL-3, a matrix metalloproteinase inhibitor, in patients with refractory metastatic cancer. Rudek M A, Figg W D, Dyer V, Dahut W, Turner M L, Steinberg S M, Liewehr D J, Kohler D R, Pluda J M, Reed E J CLIN ONCOL 2001 19 2 584-592
409854 Pharmacodynamic studies of Col-3, a novel matrix metalloproteinase inhibitor, in patients with advanced cancer. Munoz Mateu M, de'Grafenried L, Eckhardt S, Malik S. Rizzo J, Kuhn J, Rowinsky E, Hidalgo M PROC AM SOC CLIN ONCOL 2001 20 Abs 302
417817 CollaGenex Pharmaceuticals announces initiation of phase II clinical trial in Kaposi's sarcoma with proprietary angiogenesis inhibitor; AIDS Malignancy Consortium sponsored by the National Cancer Institute opens a multicenter study to determine the response rate of COL-3 (Metastat) in patients with HIV-related Kaposi's sarcoma. CollaGenex Pharmaceuticals Inc PRESS RELEASE 2001 Aug. 2
423317 Matrix metalloproteinases as targets for therapy in Kaposi's sarcoma. Fingleton B, Matrisian L M CURR OPIN ONCOL 2001 13 5 368-373

428456 The role of matrix metalloproteinases in tumor angiogenesis and tumor metastasis. John. A, Tuszynski G *PATHOL ONCOL RES* 2001 7 1 14-23

439895 Matrix metalloproteinases. Nagase H, Woessner J F *J BIOL CHEM* 1999 274 31 21491-21494

442743 CollaGenex Pharmaceuticals announces publication of Metastat phase I results in Journal of Clinical Oncology. CollaGenex Pharmaceuticals Inc *PRESS RELEASE* 2002 Mar. 7

467178 Discovery and CollaGenax collaborate to develop novel treatments for respiratory diseases. Discovery Laboratories inc *PRESS RELEASE* 2002 Oct. 17

481027 CollaGenex Pharmaceuticals announces US patent for new IMPACS compound. CollaGenex Pharmaceuticals inc *PRESS RELEASE* 2003 Mar. 6

483919 CollaGenex Pharmaceuticals announces phase II Metastat clinical trial in Kaposi's sarcoma fully enrolled. CollaGenex Pharmaceuticals Inc *PRESS RELEASE* 2003 Mar. 28

486824 Targeting the tumor microenvironment with chemically modified tetracyclines: Inhibition of laminin 5 γ2 chain promigratory fragments and vasculogenic mimicry. Seftor R E B, Seftor E A. Kirschmann D A, Hendrix M J C *MOL CANCER THER* 2002 113 1173-1179

436833 Inhibition of cell proliferation, invasion, tumor growth and metastasis by an oral non-antimicrobial tetracycline analog (COL-3) in a metastatic prostate cancer model. Lokeshwar B L, Seizer M G, Zhu B Q, Block N L, Golub L M *INT J CANCER* 2002 98 2 297-309

486836 Matrix metalloproteinase inhibitor COL-3 in the treatment of AIDS-related Kaposi's sarcoma: A phase I AIDS malignancy consortium study. Cianfrocca M, Cooley T P, Lee J Y, Rudek M A, Scadden D T, Ratner L, Pluda J M, Figg W D, Krown S E, Dezube 3J *J CLIN ONCOL* 2002 20 1 153-159

493831 Drug status validation: Marimastat. British Biotech pic *COMPANY COMMUNICATION* 2003 Jun. 13

494695 Application of chemically modified tetracyclines (CMTs) in experimental models of cancer and arthritis. Seftor E A, Seftor R E, Nieva D R, Hendrix M J *ADVANCES DENTAL RESEARCH* 1998 12 2 103-110

494714 High-performance liquid chromatography with mass spectrometry detection for quantitating COL-3, a chemically modified tetracycline, in human plasma. Rudek M A, March C L, Bauer K S Jr, Pluda J M, Figg W D *J PHARM BIOMED ANAL* 2000 22 5 1003-1014

494720 Potential application of a chemically modified non-antimicrobial tetracycline (CMT-3) against metastatic prostate cancer. Lokeshwar B L, Houston-Clark H L, Selzer M G, Block N L, Golub L M *ADVANCES DENTAL RESEARCH* 1998 12 2 97-102

494725 Effects of tetracyclines on angiogenesis in vitro. Fife R S, Sledge G W Jr, Sissons S, Zerler 3 *CANCER LETT* 2000 153 1-2 75-78

494736 Evidence for dissolution rate-limited absorption of COL-3, a matrix metalloproteinase inhibitor, leading to the irregular absorption profile in rats after oral administration. Li J, Huynh H, Chan E *PHARM RES* 2002 19 11 1655-1662

494740 Effect of doxycycline on immune response in mice. Bellahsene A, Forsgren A *INFECT IMMUN* 1985 48 2 555-559

494744 Comparative toxicity of oxytetracycline and its semisynthetic derivatives, methacycline and doxycycline. Zei'tser I Z, Balabanova E L, Lapchinskaia A V, Anufrieva R G, Gerasimova S S *ANTIBIOT KHIMIOTER* 1978 23 6 533-536

494756 COL-3 in treating patients with progressive or recurrent brain tumors. *INTERNET SITE* 2003 Jun. 24

494759 Reversible sideroblastic anemia associated with the tetracycline analogue COL-3. Rudek M A, Home M, Figg W D, Dahut W, Dyer V, Pluda J M, Reed E *AM J HEMATOL* 2001 67 1 51-53

494762 Drug-induced lupus associated with COL-3: Report of 3 cases. Ghate J V, Turner M L, Rudek M A, Figg W D, Dahut W, Dyer V, Pluda J M, Reed E *ARCH DERMATOL* 2001 137 4 471-474

494768 Matrix metalloproteinase inhibitors and cancer: Trials and tribulations. Coussens L M, Fingleton B, Matrisian L M *SCIENCE* 2002 29 5564 2387-2392

494782 A phase I trial of doxocycline (Doxy) in patients with cancer. Gordon M S, Battiato L A, Jones D, Roth B J, Harrison-Mann 3, Fife R, Collins M, Sledge G W Jr *PROC AM SOC CLIN ONCOL* 1997 16 Abs 794

495635 The inhibition of metalloproteinases as a therapeutic target in rheumatoid arthritis and osteoarthritis. Bigg H F, Rowan A D *CURR OPIN PHARMACOL* 2001 1 3 314-320

495640 Matrix metalloproteinases in vascular remodeling and atherogenesis: The good, the bad, and the ugly. Galis Z S, Khatri J J *CIRC RES* 2002 90 3 251-262

495642 Proteinases in chronic obstructive pulmonary disease. Shapiro S D *BIOCHEM SOC TRANS* 2002 30 2 98-102

495646 The 72-kDa and the 92-kDa gelatinases, but not their inhibitors TIMP-1 and TIMP-2, are expressed in early psoriatic lesions. Feliciani C, Vitullo P, D'orazi G, Paimirotta R, Amerio P, Amerio S M, Coscione G, Amerio P L, Modesti A *EXP DERMATOL* 1997 6 6 321-327

495649 Matrix metalloproteinases: Multifunctional effectors of inflammation in multiple sclerosis and bacterial meningitis. Leppert 0, Lindberg R L, Kappos L, Leib S L *BRAIN RES REV* 2001 36 2-3 249-257

498815 Collagenex Pharmaceuticals initiates phase II clinical study to evaluate COL-3 as a treatment for rosacea. CollaGenex Pharmaceuticals Inc *PRESS RELEASE* 2003 Jul. 24

501081 Collagenase in periodontal diseases. Birkedal-Hansen H In: *COLLAGENASE NORMAL PATHOLOGICAL CONNECTIVE TISSUES* Wolley D E, Evanson J (Eds), John Wiley and Sons, Chinchester UK 1980

501235 Preclinical and clinical pharmacokinetics of COL-3. Rudek M A, Dyer V D, Hamilton J M, Pluda J, Reed E, Figg W D *PHARMACOTHERAPY* 1998 18 5 1147

505156 Drug-induced cutaneous photosensitivity: incidence, mechanism, prevention and management. Moore D E *DRUG SAF* 2002 25 5 345-372

505157 Drug-induced cutaneous photosensitivity: Some drugs warrant routine precautions. *PRESCRIBE INT* 2000 9 48:117-122.

What is claimed is:

1. A method for slowing progression of a degenerative disc disease in a human subject suffering from the degenerative disc disease which comprises administering to the subject a pharmaceutical composition comprising a pharmaceutically acceptable carrier and a 4-dedimethyltetracycline homolog or analog, in conjunction with a surgical procedure which results in the intervertebral discs of the subject being accessible to the 4-dedimethyltetracycline homolog or analog, wherein said pharmaceutical composition is administered in an amount effective to slow the progression of the degenerative disc disease, wherein the surgical procedure comprises microdiscectomy, and wherein said 4-dedimethyltetracycline homolog or analog is selected from the group consisting of 4-dedimethylaminotetracycline, 4-dedimethylaminosancycline (6-demethyl-6-deoxy-4-dedimethylaminotetracycline),
4-dedimethylaminominocycline (7-dimethylamino-4-dedimethylaminotetracycline), and
4-dedimethylaminodoxycycline (5-hydroxy-6-deoxy-4-dedimethylaminotetracycline);

is present in said pharmaceutical composition at a concentration of 0.1% to 5% by weight of the composition; and is administered in an amount between 0.1 mg/kg and 30 mg/kg body weight of the subject.

2. The method of claim 1, wherein the amount effective to treat the subject is also effective to reduce pain concomitant with the degenerative disc disease.

3. The method of claim 1, wherein the pharmaceutically acceptable carrier comprises a biopolymer.

4. The method of claim 3, wherein the biopolymer comprises hyaluronic acid or a pharmaceutically acceptable salt or ester thereof.

5. The method of claim 1, wherein the pharmaceutically acceptable carrier comprises a hydrogel.

6. The method of claim 1, wherein the 4-dedimethyltetracycline homolog or analog is present at a concentration of 0.1% to 1.0% by weight.

7. The method of any of claim 1, wherein the pharmaceutical composition is administered by means of a needle or a cannula.

8. The method of claim 1, wherein the amount of the 4-dedimethyltetracycline homolog or analog administered is between 0.3 mg/kg and 10 mg/kg body weight of the subject.

9. The method of claim 1, wherein the pharmaceutical composition is administered multiple times over a period of 30-180 days.

* * * * *